US011167095B2

(12) United States Patent
Ralph et al.

(10) Patent No.: US 11,167,095 B2
(45) Date of Patent: Nov. 9, 2021

(54) VARIABLE PITCH FLEXIBLE NEEDLE

(71) Applicant: Spiration, Inc., Redmond, WA (US)

(72) Inventors: Christopher R. Ralph, Woodinville, WA (US); Jean-Martin Baillargeon, Seattle, WA (US); Jason T. Panzenbeck, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 489 days.

(21) Appl. No.: 15/916,226

(22) Filed: Mar. 8, 2018

(65) Prior Publication Data
US 2019/0275260 A1 Sep. 12, 2019

(51) Int. Cl.
A61M 5/32 (2006.01)
A61B 10/02 (2006.01)
A61B 10/04 (2006.01)
A61B 18/14 (2006.01)
A61B 18/00 (2006.01)

(52) U.S. Cl.
CPC ......... A61M 5/329 (2013.01); A61B 10/0283 (2013.01); A61B 10/04 (2013.01); A61B 18/1477 (2013.01); A61B 2010/045 (2013.01); A61B 2018/00577 (2013.01); A61M 2210/1039 (2013.01)

(58) Field of Classification Search
CPC ............ A61B 10/0233; A61B 10/0283; A61B 2010/045; A61B 17/3415; A61B 17/3417; A61B 18/1477; A61B 18/1492; A61B 10/04; A61M 5/329
See application file for complete search history.

(56) References Cited

U.S. PATENT DOCUMENTS

| 6,656,195 | B2 | 12/2003 | Peters et al. | |
|---|---|---|---|---|
| 2011/0054487 | A1 | 3/2011 | Farnan | |
| 2012/0116382 | A1* | 5/2012 | Ku | A61B 18/1492 606/33 |
| 2012/0136350 | A1* | 5/2012 | Goshgarian | A61B 18/1492 606/41 |
| 2014/0276051 | A1* | 9/2014 | Hoffman | A61B 10/0233 600/439 |

(Continued)

Primary Examiner — Daniel L Cerioni
Assistant Examiner — Raymond P Dulman
(74) Attorney, Agent, or Firm — Clements Bernard Baratta; Frank J. Bozzo

(57) ABSTRACT

Disclosed embodiments include flexible tube assemblies, flexible needle assemblies, systems, methods of fabricating a flexible tube, and methods of fabricating a flexible needle. In an illustrative, non-limiting embodiment, a flexible tube assembly includes: a flexible tube having a proximal end with a proximal strain relief section and a distal end with a distal strain relief section, the proximal strain relief section being located between the proximal end and the distal strain relief section and the distal strain relief section being located between the distal end and the proximal strain relief section, the distal end defining an opening therein, at least a portion of at least one of the proximal strain relief section and the distal strain relief section defining therein a spiral cut with a continuously variable pitch; and tubing disposed in an airtight manner over an exterior surface of the flexible tube at least the portion of the at least one of the proximal strain relief section and the distal strain relief section defining therein the spiral cut with a continuously variable pitch.

11 Claims, 11 Drawing Sheets

(56) References Cited

U.S. PATENT DOCUMENTS

2015/0342580 A1* 12/2015 Clancy .................. A61B 10/04
600/567
2017/0319776 A1* 11/2017 Eisner ................. A61M 3/0295
2019/0231424 A1* 8/2019 Davies .................. A61N 1/056

* cited by examiner

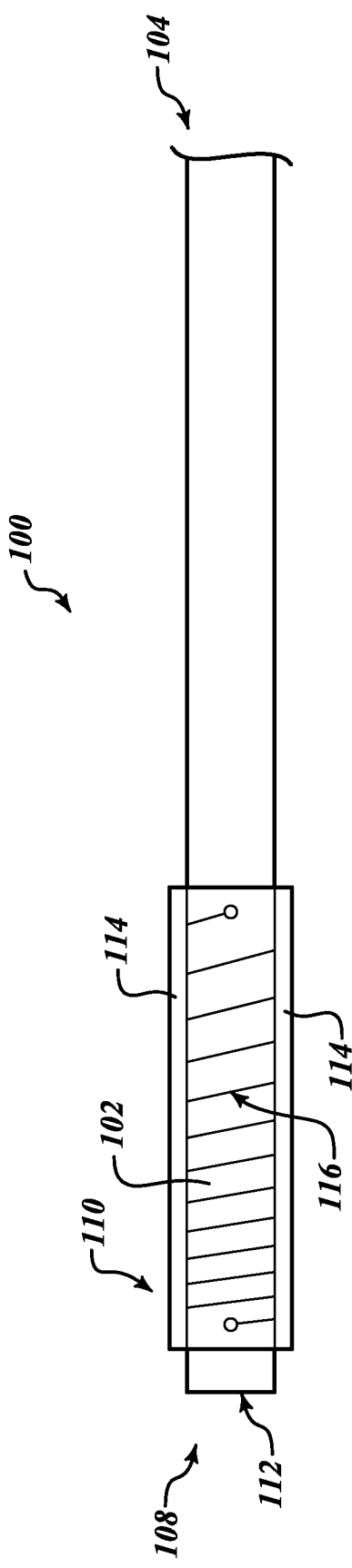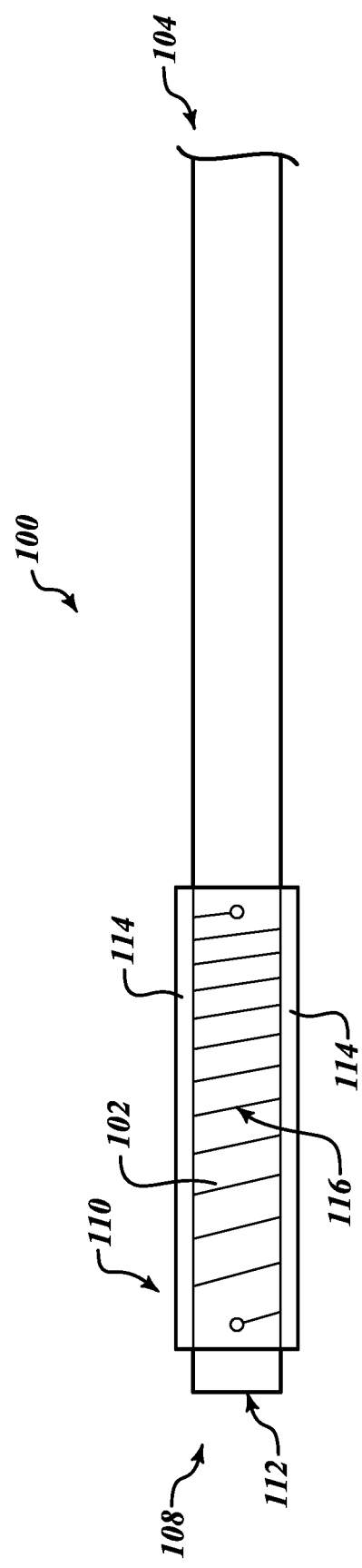

Dispose heat-shrink tubing in an airtight manner over an exterior surface of the flexible tube at least the portion of the at least one of the proximal strain relief section and the distal strain relief section defining therein the spiral cut with a continuously variable pitch ⟶ 612

Dispose heat-shrink tubing in an airtight manner over an exterior surface of the flexible needle from the proximal end to the distal end ~716

712

FIG. 7B

VARIABLE PITCH FLEXIBLE NEEDLE

RELATED APPLICATIONS

Disclosed subject matter in this application is related to subject matter disclosed in U.S. patent application Ser. No. 13/778,049, filed Feb. 26, 2013, entitled "Lung Biopsy Needle," and published on Aug. 29, 2013 as U.S. Patent Application Publication No. 2013/0225997, the entire contents of which are hereby incorporated by this reference.

FIELD

Disclosed embodiments relate to a flexible needle for biopsying tissue and/or delivering fluid, medicine, or other material to regions of interest.

BACKGROUND

The statements in this section merely provide background information related to the present disclosure and may not constitute prior art.

Early diagnosis of potentially cancerous tissue is an important step in the treatment of cancer because, the sooner that cancerous tissue can be treated, and the better the patient's chances are for survival. Typical diagnostic procedures involve biopsying tissue at a site of interest. In the case of lungs, lung cancer can be difficult to diagnose due to the difficulties in accessing airways near areas of interest. Areas of interest may present as lung nodules-small tissue masses in the lung that may range in size between 5-25 mm—that typically are biopsied to ascertain whether the tissue therein is cancerous or otherwise diseased.

Existing systems typically are constrained by difficulties in accessing lung nodules, especially in the smaller peripheral airways that may be too narrow to accommodate larger catheters and biopsy apparatuses. Further, biopsy needles normally are straight and relatively inflexible. Thus, the biopsy needles can limit the articulation of a bronchoscope or can be difficult to pass through a working channel of a bronchoscope when the bronchoscope is articulated around a tight corner. In some instances, the material of the needle may inelastically yield, which can result in a bent needle that is difficult to control. In addition, the straight biopsy needles obtain samples along an axis of the needle through back and forth cycling of the needle. Thus, obtaining multiple samples from different regions of a single nodule, for example, can be difficult and can require repeated repositioning of the bronchoscope or guide sheath, for example.

Conventional flexible needle technology can help permit better access to regions of interest, such as lymph nodes, by helping allow greater endoscope angulation. Needle flexibility is typically achieved via a spiral hole that is laser cut through the needle's wall along the needle's length at its distal end. The laser cut section of the flexible needle typically is covered by a thin layer of heatshrink material to prevent creation of an open path between the interior of the needle and the exterior of the needle through the needle's wall (hereinafter referred to as a "shunt") and to allow for tissue aspiration via a vacuum from the needle tip through its entire length.

With high needle angulations achieved due to the increased flexibility, the heatshrink material may be under compression or tension stress. That stress is the greatest at both ends where the laser cut ends and the needle tube becomes inflexible (that is, solid) again because the heatshrink needs to go past the laser cut to avoid creation of a shunt and to ensure proper coverage. The high stresses where the laser cut ends may possibly lead to tearing or cracking of the heatshrink, thereby helping to create a shunt and helping lead to the loss of vacuum, thereby adversely impacting the needle's ability to aspirate tissue.

SUMMARY

Disclosed embodiments include flexible tube assemblies, flexible needle assemblies, systems, methods of fabricating a flexible tube, and methods of fabricating a flexible needle.

In an illustrative, non-limiting embodiment, a flexible tube assembly includes: a flexible tube having a proximal end with a proximal strain relief section and a distal end with a distal strain relief section, the proximal strain relief section being located between the proximal end and the distal strain relief section and the distal strain relief section being located between the distal end and the proximal strain relief section, the distal end defining an opening therein, at least a portion of at least one of the proximal strain relief section and the distal strain relief section defining therein a spiral cut with a continuously variable pitch; and tubing disposed in an airtight manner over an exterior surface of the flexible tube at least the portion of the at least one of the proximal strain relief section and the distal strain relief section defining therein the spiral cut with a continuously variable pitch.

In another illustrative, non-limiting embodiment, a flexible needle assembly includes: a flexible needle having a proximal end with a proximal strain relief section, a distal end with a distal strain relief section, and an intermediate section disposed intermediate the proximal end and the distal end, the proximal strain relief section being located between the proximal end and the intermediate section and the distal strain relief section being located between the distal end and the intermediate section, the distal end defining a tip configured to pierce tissue, the proximal strain relief section defining therein a spiral cut with a continuously variable pitch that varies from a first pitch value to a second pitch value that is greater than the first pitch value, the intermediate section defining therein the spiral cut with a substantially constant pitch with the second pitch value, the distal strain relief section defining therein the spiral cut with a continuously variable pitch that varies from the second pitch value to a third pitch value that is greater than the second pitch value; and tubing disposed in an airtight manner over an exterior surface of the flexible needle from the proximal end to the distal end.

In another illustrative, non-limiting embodiment, a system includes: a sheath; a flexible tube assembly disposed in the sheath, the flexible tube assembly including: a flexible tube having a proximal end with a proximal strain relief section and a distal end with a distal strain relief section, the proximal strain relief section being located between the proximal end and the distal strain relief section and the distal strain relief section being located between the distal end and the proximal strain relief section, the distal end defining an opening therein, at least a portion of at least one of the proximal strain relief section and the distal strain relief section defining therein a spiral cut with a continuously variable pitch; and tubing disposed in an airtight manner over an exterior surface of the flexible tube at least the portion of the at least one of the proximal strain relief section and the distal strain relief section defining therein the spiral cut with a continuously variable pitch; and a medical device operatively coupled to the flexible tube.

In another illustrative, non-limiting embodiment, a method of fabricating a flexible tube assembly includes:

providing a flexible tube having a proximal end with a proximal strain relief section and a distal end with a distal strain relief section, the proximal strain relief section being located between the proximal end and the distal strain relief section and the distal strain relief section being located between the distal end and the proximal strain relief section, the distal end defining an opening therein; defining in at least a portion of at least one of the proximal strain relief section and the distal strain relief section a spiral cut with a continuously variable pitch; and disposing tubing in an airtight manner over an exterior surface of the flexible tube at least the portion of the at least one of the proximal strain relief section and the distal strain relief section defining therein the spiral cut with a continuously variable pitch.

In another illustrative, non-limiting embodiment, a method of fabricating a flexible needle assembly includes: providing a flexible needle having a proximal end with a proximal strain relief section and a distal end with a distal strain relief section and an intermediate section disposed intermediate the proximal end and the distal end, the proximal strain relief section being located between the proximal end and the intermediate section and the distal strain relief section being located between the distal end and the intermediate section, the distal end defining a tip configured to pierce tissue; defining in the proximal strain relief section a spiral cut with a continuously variable pitch that varies from a first pitch value to a second pitch value that is greater than the first pitch value; defining in the intermediate section a spiral cut with a substantially constant pitch with the second pitch value; defining in the distal strain relief section a spiral cut with a continuously variable pitch that varies from the second pitch value to a third pitch value that is greater than the second pitch value; and disposing tubing in an airtight manner over an exterior surface of the flexible needle from the proximal end to the distal end.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIG. 2C is a side plan view in partial schematic form and in partial cutaway of another embodiment of a flexible tube assembly.

FIG. 2D is a side plan view in partial schematic form and in partial cutaway of another embodiment of a flexible tube assembly.

FIG. 6B illustrates details of the flowchart of FIG. 6A.

FIG. 7B illustrates details of the flowchart of FIG. 7A.

DETAILED DESCRIPTION

The following description is merely exemplary in nature and is not intended to limit the present disclosure, application, or uses.

Various embodiments of a flexible tube assembly, a flexible needle assemble, and a transbronchial needle aspiration system and its related components and parts will now be described with reference to the accompanying figures. The terminology used in the description presented herein is not intended to be interpreted in any limited or restricted manner. Rather, the terminology is simply used in conjunction with a detailed description of embodiments of the assemblies, systems, methods and related components. Furthermore, embodiments may comprise several novel features, no single one of which is solely responsible for its desirable attributes or is believed to be essential to practicing the disclosed embodiments herein described. For example, while references may be made herein to using the embodiments described herein with terms such as "lung," "airway," "nodule," and so forth, these terms are broad and the embodiments described may be used without limitation and unless otherwise indicated can be used to access to other vessels, passages, lumens, body cavities, tissues, and organs present in humans and animals. For example, lumens such those in as the gastrointestinal system (that is, intestines) may be accessed with the embodiments described herein.

Figure 1:
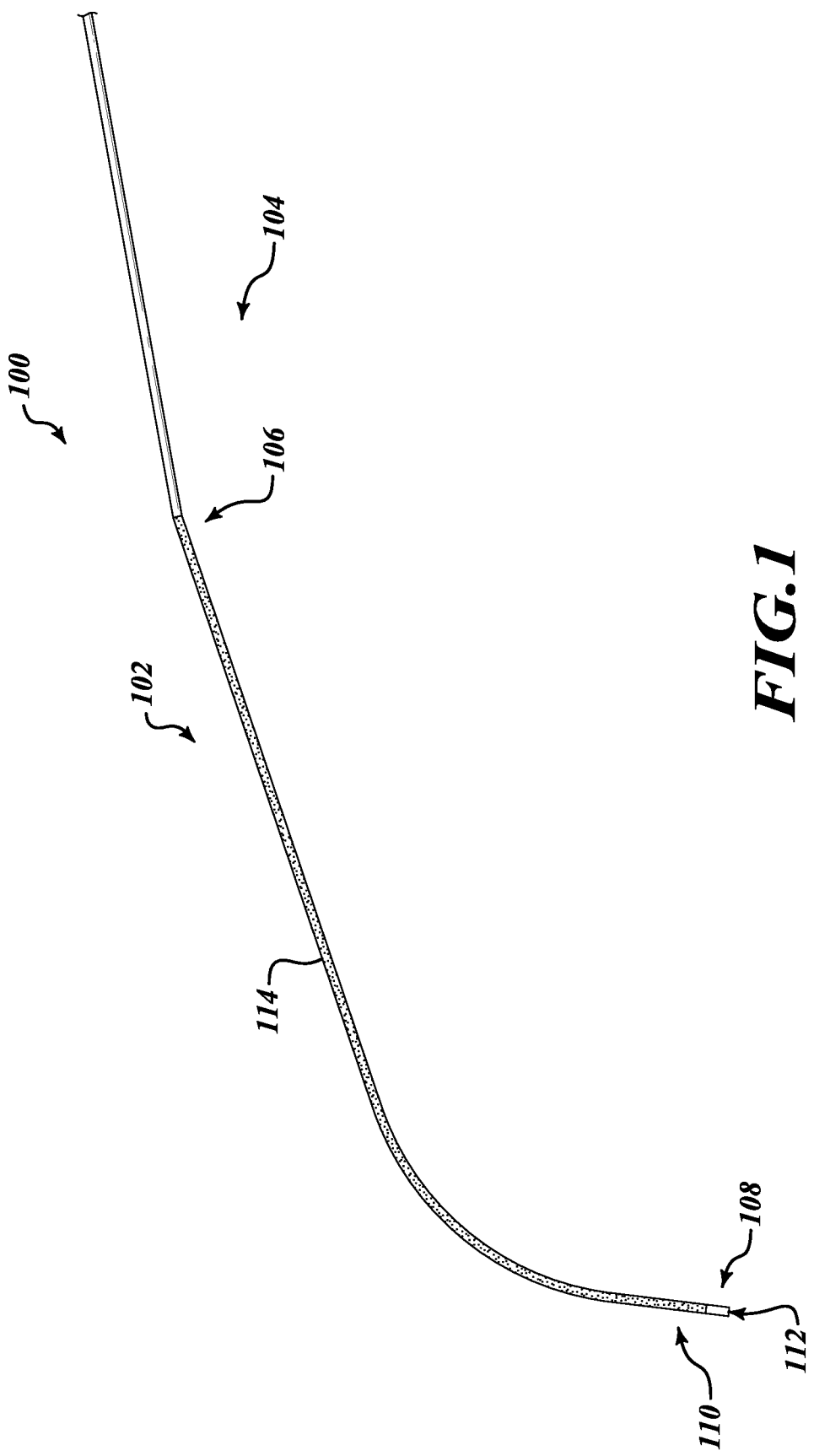
FIG. 1 is a perspective view in partial schematic form of an illustrative flexible tube assembly.

Given by way of overview and referring to FIG. 1, an illustrative, non-limiting embodiment of a flexible tube assembly 100 is shown. As will be discussed herein, embodiments of this flexible tube assembly 100, as well as the other embodiments described herein, may be used in conjunction with existing systems and methods for locating, navigating to, and biopsying regions (e.g., lung nodules, lymph nodes) of interest and/or delivering fluid, medicine, or other material to regions of interest. Use of embodiments in which the flexible tube assembly 100 is embodied as a flexible needle can permit biopsying tissue and cells in a much larger area and over a wider range of angles compared to existing systems, and certain embodiments allow for greater articulation of a bronchoscope or endoscope so as to gain access to tortuous areas of the anatomy. Accordingly, the use of such embodiments can provide increased sample quality, greater diagnostic yields, and a reduction of erroneous diagnostic results (that is, false positives or negatives). It will be noted that although bronchoscopes are referred to herein, other endoscopes may be usable (such as gastric endoscopes and colonoscopes). As such, other lumens may be explored, navigated to, and biopsied using the embodiments described herein.

Still by way of overview and still referring to FIG. 1, in an illustrative, non-limiting embodiment of the flexible tube assembly 100 a flexible tube 102 has a proximal end 104 with a proximal strain relief section 106 and a distal end 108 with a distal strain relief section 110. The proximal strain relief section 106 is located between the proximal end 104 and the distal strain relief section 110 and the distal strain relief section 110 is located between the distal end 108 and the proximal strain relief section106. The distal end 108 defines an opening 112 therein. At least a portion of the proximal strain relief section 106 and/or the distal strain relief section 110 defines therein a spiral cut (not shown in FIG. 1) having a continuously variable pitch. Tubing 114 is disposed in an airtight manner over an exterior surface of the flexible tube 102 from at least the portion of the at least one of the proximal strain relief section and the distal strain relief section defining therein the spiral cut with a continuously variable pitch.

Now that an overview has been provided, details will be set forth below by way of non-limiting examples and not of limitation.

Still referring to FIG. 1, the tube 102 may be made of any suitable material and may have any size as desired for a particular application. Given by way of non-limiting example, the tube 102 may be made of metal or metal alloy, such as stainless steel like American Iron and Steel Institute ("AISI") type 304 stainless steel, other stainless steels, plastics, nitinol or the like. Also by way of non-limiting example, the tube 102 may be made from a hypotube. In such embodiments, the tube 102 may be a 19 gauge hypotube, a 20 gauge hypotube, a 21 gauge hypotube, a 22 gauge hypotube, a 25 gauge hypotube, a 27 gauge hypotube, or the like, depending on size and flexibility constraints of particular applications. In such embodiments, the hypotube suitably is constructed to be relatively smooth along at least a proximal portion such that when introduced into a device such as a catheter lumen, for example but without limitation, the hypotube is able to relatively freely slide, rotate, or otherwise move along the lumen.

Still referring to FIG. 1, in various embodiments the tubing 114 includes heatshrink tubing. In such embodiments, the heatshrink tubing 114 is disposed in an airtight manner over an exterior surface of the flexible tube 102 from at least the portion of the proximal strain relief section 106 and/or the distal strain relief section 108 that defines therein a spiral cut with a continuously variable pitch. That is, in such embodiments the heatshrink tubing 114 covers the entirety of the spiral cut wherever it is defined and the heatshrink tubing 114 extends past the end of the spiral cut. As such, the heatshrink tubing 114 can help to prevent creation of a shunt, can help to allow for tissue aspiration via a vacuum from the needle tip (in embodiments in which the tube assembly 100 is a flexible needle assembly) through the entire length of the flexible tube assembly 100, and can also help in transport of fluid, medicine, or other material to regions of interest through the entire length of the flexible tube assembly 100 and delivery thereof through the opening 112 in some other embodiments. The heatshrink tubing 114 can also act as an electrical insulator in embodiments in which the flexible tube 102 functions as an electrode.

It will be appreciated that flexibility of the flexible tube 102 may be tailored as desired for a particular application. The flexibility can be changed, for example, by modifying the thickness of the wall of the flexible tube 102, the materials used therein, and the spacing, pitch, and angle between the lines in the spiral cut. In some embodiments, the lines in the spiral cut are cut with a thickness between about 0.0010 and about 0.0025 inches, and suitably in a range between about 0.0015 and about 0.0020 inches. It will be appreciated that the spiral cut may have any pitch values as suitable for providing desired flexibility for a given application. Higher pitch values result in less flexibility of the tube 102 than do lower pitch values and lower pitch values result in more flexibility of the tube 102 than do higher pitch values. In some embodiments, portions of the spiral cut may have pitch values as high as 0.120 or 0.150 and in some embodiments portions of the spiral cut may have pitch values as low 0.040, 0.060, or 0.080, as desired for a particular application.

Figure 2A:
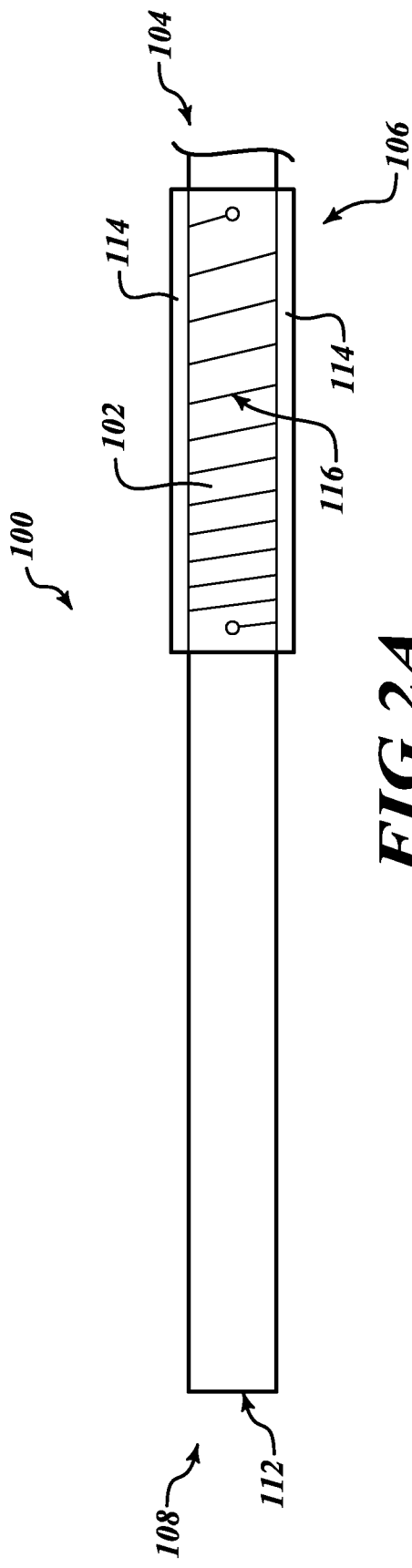
FIG. 2A is a side plan view in partial schematic form and in partial cutaway of an embodiment of a flexible tube assembly.
Figure 2B:
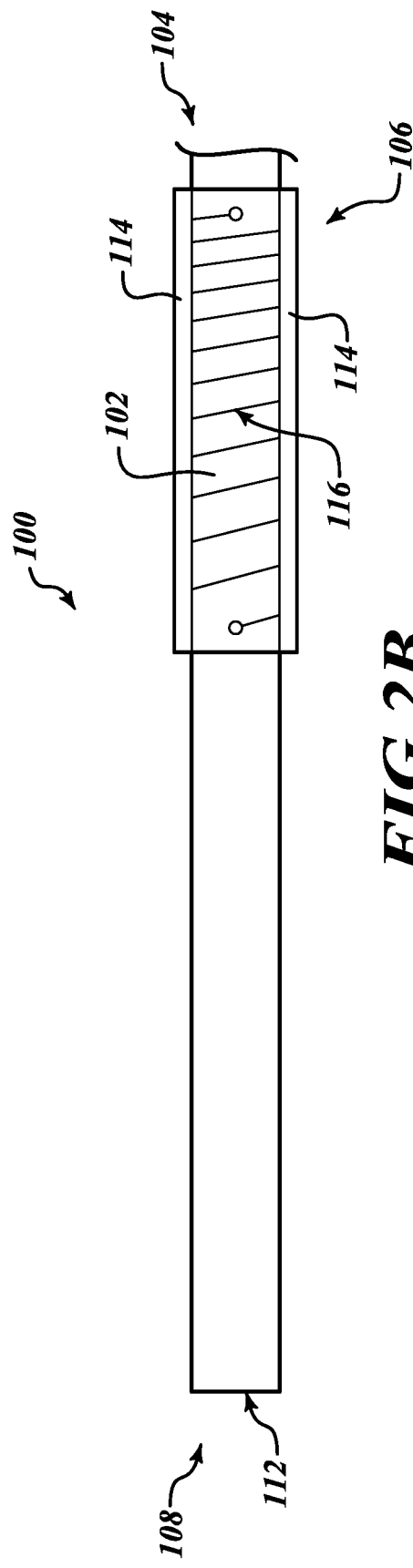
FIG. 2B is a side plan view in partial schematic form and in partial cutaway of another embodiment of a flexible tube assembly.

It will be appreciated that several embodiments of the flexible tube assembly 100 may be suited for various applications as desired. Given by way of non-limiting example and referring to FIGS. 2A-2D, in some embodiments flexibility may be desired in only one portion of the flexible tube assembly 100. In some of these embodiments the spiral cut 116 may be defined in only the proximal strain relief section 106 (FIGS. 2A and 2B) or the distal strain relief section 110 (FIGS. 2C and 2D), depending upon where flexibility is desired. In some of these embodiments, pitch value of the spiral cut 116 may continuously decrease as the spiral cut 116 travels in a direction from the proximal end 104 toward the distal end 108 (FIGS. 2A and 2C). In such embodiments, the lines in the spiral cut 116 continuously become closer together and the tube 102 becomes more flexible as the spiral cut 116 travels in a direction from the proximal end 104 toward the distal end 108. In some other of these embodiments, pitch value of the spiral cut 116 may continuously increase as the spiral cut 116 travels in a direction from the proximal end 104 toward the distal end 108 (FIGS. 2B and 2D). In such embodiments, the lines in the spiral cut 116 continuously become farther apart and the tube 102 becomes less flexible as the spiral cut 116 travels in a direction from the proximal end 104 toward the distal end 108.

In some other embodiments, flexibility may be desired in more than one portion of the flexible tube assembly 100. In such embodiments, the spiral cut 116 may be defined in both the proximal strain relief section 106 and the distal strain relief section 110. In some of these embodiments and referring now to FIGS. 3A and 3B, the proximal strain relief section 106 and the distal strain relief section 110 are contiguous. In these embodiments, the proximal strain relief section 106 defines therein the spiral cut 116 with a continuously variable pitch that continuously varies from a pitch value $PV_1$ adjacent the proximal end 104 to a pitch value $PV_2$ that is different from the pitch value $PV_1$ at a location intermediate the proximal end 104 and the distal end 108. Also, the distal strain relief section 110 defines therein the spiral cut 116 with a continuously variable pitch that continuously varies from the pitch value $PV_2$ at the location intermediate the proximal end 104 and the distal end 108 to a pitch value that is different from the pitch value $PV_2$.

Figure 3A:
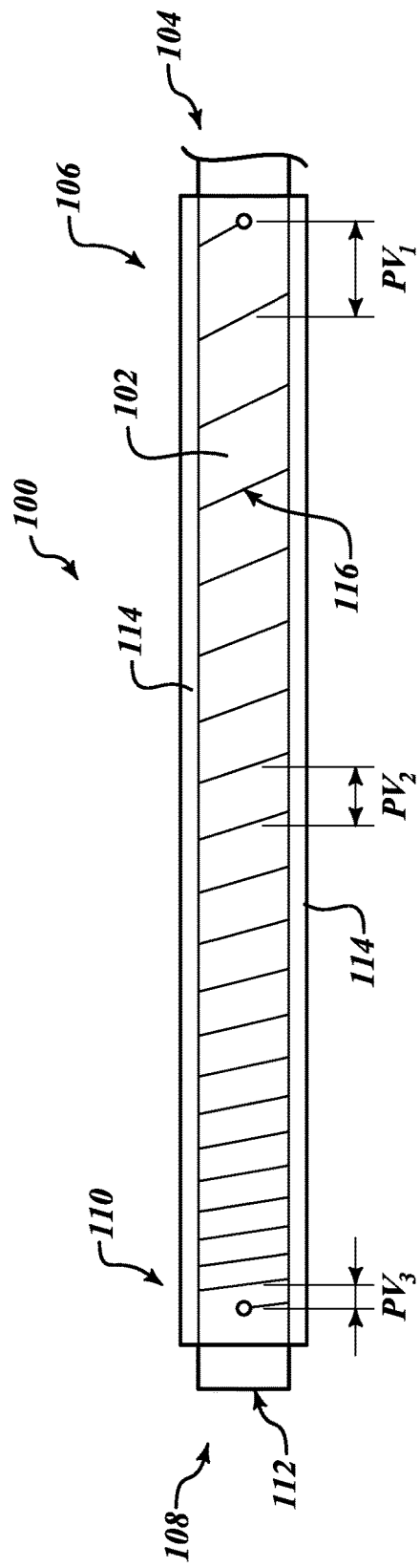
FIG. 3A is a side plan view in partial schematic form and in partial cutaway of another embodiment of a flexible tube assembly.

As shown in FIG. 3A, in one such embodiment the pitch value $PV_1$ is greater than the pitch value $PV_2$ and the pitch value $PV_3$ is less than the pitch value $PV_2$. That is, pitch value of the spiral cut 116 continuously decreases as the spiral cut 116 travels in a direction from the proximal end 104 toward the distal end 108. The lines in the spiral cut 116 continuously become closer together and the tube 102 becomes more flexible as the spiral cut 116 travels in a direction from the proximal end 104 toward the distal end 108, with the tube 102 being most flexible at the end of the spiral cut 116 near the distal end 108.

Figure 3B:
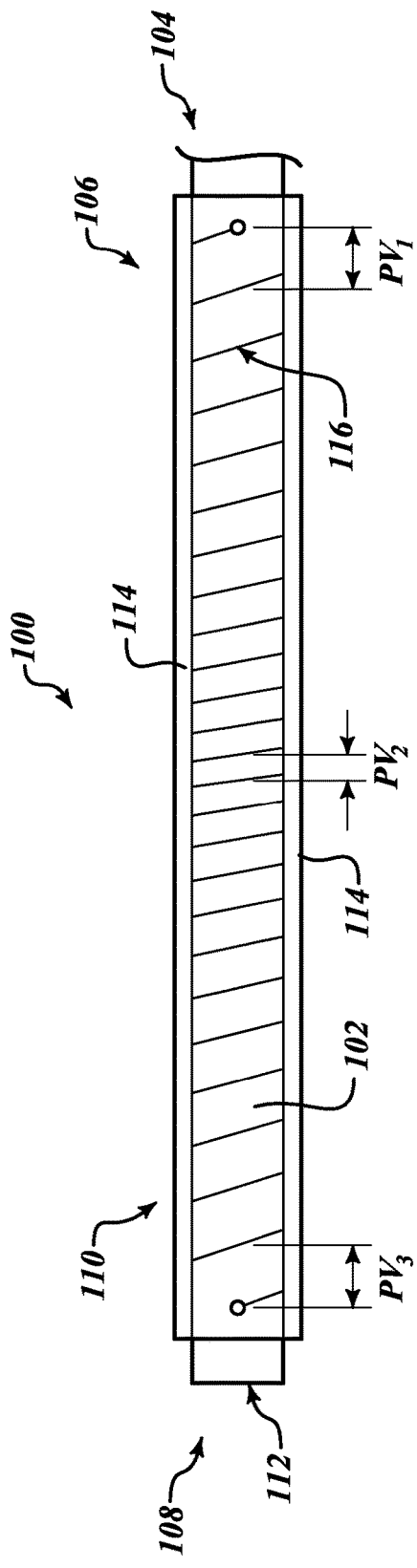
FIG. 3B is a side plan view in partial schematic form and in partial cutaway of another embodiment of a flexible tube assembly.

As shown in FIG. 3B, in another such embodiment the pitch value $PV_1$ is greater than the pitch value $PV_2$ and the pitch value $PV_3$ is greater than the pitch value $PV_2$. That is, pitch value of the spiral cut 116 continuously decreases as the spiral cut 116 travels to the location intermediate the proximal end 104 and the distal end 108 in a direction from the proximal end 104 toward the distal end 108. Pitch value of the spiral cut 116 continuously increases as the spiral cut 116 travels from the location intermediate the proximal end 104 and the distal end 108 in a direction from the proximal end 104 toward the distal end 108. The lines in the spiral cut 116 are closest together at the location intermediate the proximal end 104 and the distal end 108 and the tube 102 is most flexible at the location intermediate the proximal end 104 and the distal end 108.

Figure 4:
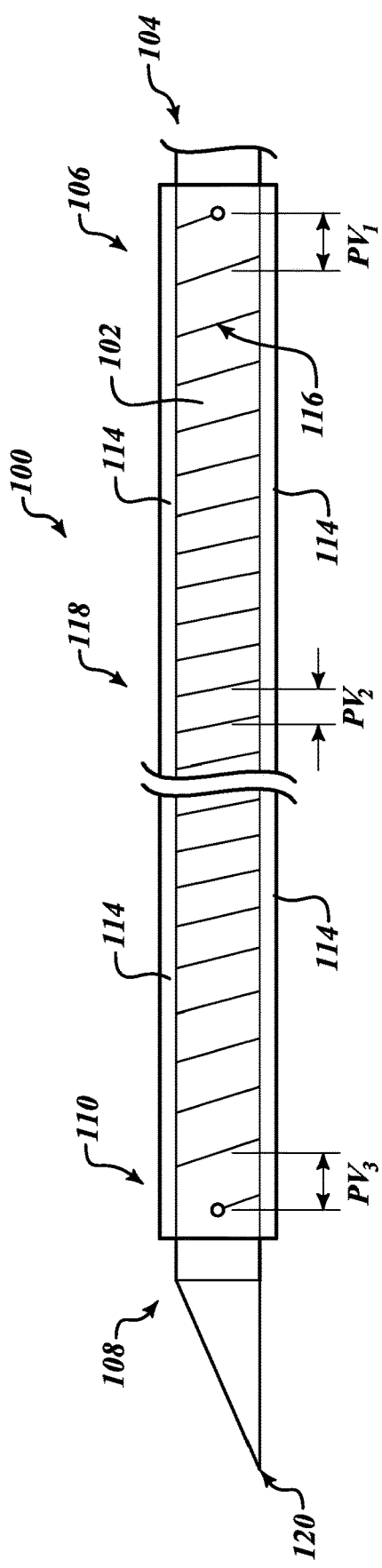
FIG. 4 is a side plan view in partial schematic form and in partial cutaway of another embodiment of a flexible tube assembly configured as a flexible needle assembly.

Referring additionally to FIG. 4, in some embodiments the flexible tube 102 has an intermediate section 118 disposed intermediate the proximal end 104 and the distal end 108. In some such embodiments, the intermediate section 118 defines therein the spiral cut with a substantially constant pitch that has the pitch value $PV_2$. In some embodiments the pitch value $PV_1$ is greater than the pitch value $PV_2$ and the pitch value $PV_3$ is greater than the pitch value $PV_2$. That is, pitch value of the spiral cut 116 continuously decreases as the spiral cut 116 travels to intermediate section 118 in a direction from the proximal end 104 toward the distal end 108. Pitch value of the spiral cut 116 continuously increases as the spiral cut 116 travels from the intermediate section 118 in a direction from the proximal end 104 toward the distal end 108. The lines in the spiral cut 116 are closest together in the intermediate section 118 and the tube 102 is most flexible in the intermediate section 118.

In some embodiments the distal end 108 defines a piercing tip 120 that is configured to pierce tissue. In such embodiments, the flexible tube assembly 100 suitably is configured as a flexible needle. In some embodiments the flexible tube assembly 100 (in this case configured as a flexible needle) may be associated with a bronchoscope or endoscope. As is known, the active section of a bronchoscope or endoscope entails the most flexibility in their applications. By locating the intermediate section 118 within the active section of the bronchoscope or endoscope, the flexible tube assembly 100 (configured as a flexible needle) can help contribute to flexibility of a bronchoscope or endoscope. As such, the flexible tube assembly 100 (configured as a flexible needle) can help contribute to ability of a bronchoscope or endoscope to reach and aspirate tissue from regions of interest that may be difficult to reach, such as lymph nodes.

Thus, it will be appreciated that length of the proximal strain relief section 106, length of the distal strain relief section 110, pitch value of the spiral cut 116 in the proximal strain relief section 106, and pitch value of the spiral cut 116 in the distal strain relief section 110 may be selected as desired for flexibility of a particular application.

Figure 5:
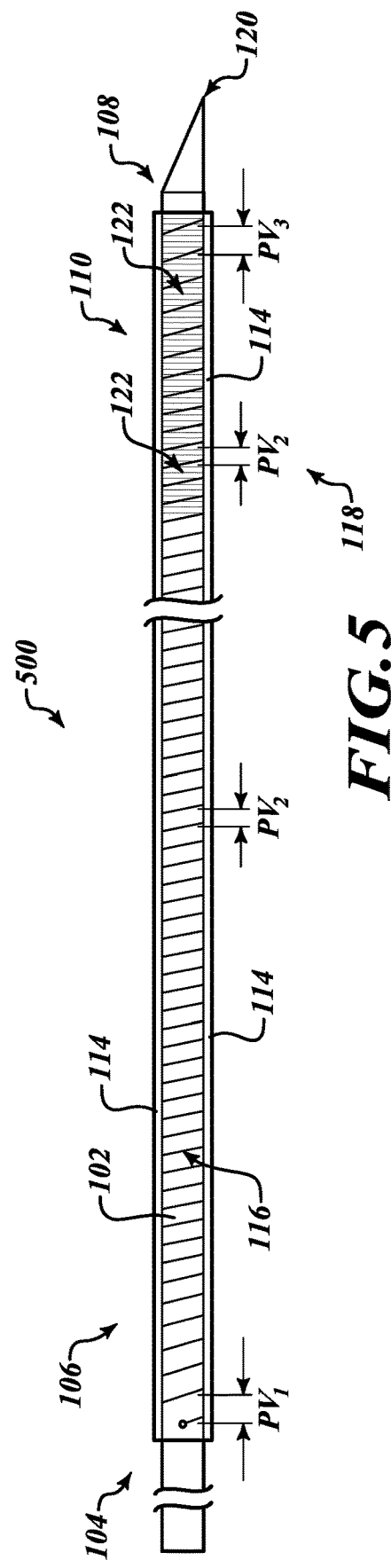
FIG. 5 is a side plan view in partial schematic form and in partial cutaway of an embodiment of a flexible needle assembly.

Referring additionally to FIG. 5, an illustrative flexible needle assembly 500 is representative of a flexible needle application of the flexible tube assembly 100 (configured as a flexible needle) shown in FIG. 4 and described above. Details of components that have been explained above, as indicated by like reference numbers, need not be repeated for an understanding of disclosed subject matter.

In an illustrative, non-limiting embodiment of the flexible needle assembly 500, the flexible needle 102 (that is, a needle application of the flexible tube 102 described above) has the proximal end 104 with the proximal strain relief section 106, the distal end 108 with the distal strain relief section 110, and the intermediate section 118 disposed intermediate the proximal end 104 and the distal end 108. The proximal strain relief section 106 is located between the proximal end 104 and the intermediate section 118, and the distal strain relief section 110 is located between the distal end 108 and the intermediate section 118. The distal end 108 defines the piercing tip 120 configured to pierce tissue. The proximal strain relief section 106 defines therein the spiral cut 116 with a continuously variable pitch that varies from a pitch value $PV_1$ to a pitch value $PV_2$ that is greater than the pitch value $PV_1$. The intermediate section 118 defines therein the spiral cut 116 with a substantially constant pitch with the pitch value $PV_2$. The distal strain relief section 110 defines therein the spiral cut 116 with a continuously variable pitch that varies from the pitch value $PV_2$ to a pitch value $PV_3$ that is greater than the pitch value $PV_2$. The tubing 114 is disposed in an airtight manner over the exterior surface of the flexible needle 102 from the proximal end 104 to the distal end 108. In various embodiments the tubing 114 includes heatshrink tubing.

In some embodiments, the flexible needle assembly 500 can be advanced to peripheral airways and can easily penetrate into the lung parenchyma. In some embodiments, the flexible needle assembly 500 can penetrate tissue at a depth of at least 15 mm. It will be appreciated that, in various embodiments, the flexible needle assembly 500 can penetrate tissue up to a depth of around 40 mm. In some embodiments, the distal end 108 of the flexible needle assembly 500 can articulate such that it can bend over 90 degrees relative to a more proximal portion. In some embodiments and when inserted into a bronchoscope working channel (such as the BF-P180™ bronchoscope manufactured by Olympus), the flexible needle assembly 500 can articulate at least 130 degrees when the pircing tip 120 is flush with the end of the bronchoscope. Due to its relatively low-profile construction, embodiments of the flexible needle assembly 500 may be miniaturized, in conjunction with a catheter or guide sheath, so as to fit into working channels (such as, of a bronchoscope) that are as small as or smaller than 2.0 mm. For example, certain embodiments of the flexible needle assembly 500 can be used with small guide sheaths with a minimum inner diameter of 1.7 mm.

It will be appreciated that the flexible needle 102 is desirably flexible such that a scope with which the flexible needle 102 is associated (such as a bronchoscope or an endoscope) can achieve a sufficiently large angle to aspirate tissue from a region of interest. Given by way of non-limiting example, sampling tissue from a lymph node entails approximately a ninety (90) degree bend in a bronchoscope. While the flexible needle 102 entails the flexibility discussed above, the flexible needle 102 also entails sufficient column strength to axially push and transmit enough force so the flexible needle 102 can push through tissue.

Embodiments described herein may be used with any suitable visualization device, such as an ultrasound system, a navigation system, or the like. By using the flexible needle assembly 500, access to regions of interest in the lung or in other tissues can be easier and more straightforward, because the flexible needle assembly 500 is able to articulate, bend, and/or curve to a greater degree than a straight, inflexible needle, and independently from the angle or articulation that a bronchoscope or endoscope may have at the same time. This may, for example, enable biopsying of tissue at an angle close to perpendicular from the bronchoscope. In addition, the flexible needle assembly 500 can bend in a region between the piecing tip 120 and the distal end of any protective guide sheath or catheter. In other words, the flexibility of the flexible needle assembly 500 reduces the likelihood of perforating the working channel of the bronchoscope. The increased flexibility also decreases the radial forces exerted by the distal end 108 of the flexible needle assembly 500 during navigation through the working channel of the bronchoscope, for example but without limitation.

Although ultrasound has been found to be a suitable system for visualization due to the relatively high penetration depth (at least 40 mm) of ultrasound, other systems also may be used. In some configurations, if desired a spiral ultrasound probe can be used to provide improved visualization over an ultrasound probe that provides visualization in not only a single plane but in all directions. Other systems for locating and navigating to tissues of interest, such as lung nodules and lymph nodes, may include using a bronchoscope with an optical channel, fluoroscopy, optical coherence tomography, and magnetic resonance imaging. Any other suitable navigation systems also can be used, including commercial systems using X-ray computed tomography assisted visualization (such as, for example but without limitation, the BfNavi™ system sold by Olympus and the i-Logic™ system sold by SuperDimension). It will be appreciated that, in embodiments in which a plastic material is used for the flexible needle 102, some of the previously-listed navigation systems, such as as X-ray or the like, may not be applicable.

The above context of flexibility and column strength entails an interplay between pitch value of the spiral cut 116 and gauge and material of the flexible needle 102. Regarding flexibility and pitch value, it will be appreciated that the lower the pitch value (that is, the tighter the spacing of the lines of the spiral cut 116) the more flexible the portion of the flexible needle 102. In various embodiments, the intermediate section 118 corresponds to the section of a scope (such as a bronchoscope or endoscope) associated with the flexible needle 102 that entails the highest degree of flexibility. Likewise, in various embodiments the distal end 108 entails a lower degree of flexibility (put another way, the distal end 108 is more rigid) than the intermediate section 118 to help the piercing tip 120 pierce tissue.

Accordingly, in some embodiments the pitch value in the proximal strain relief section 106 may begin toward the proximal end 104 with the pitch value $PV_1$ on the order of around 0.120 or 0.150 or so and continuously decreases toward the pitch value $PV_2$ at the intermediate section 118. Conversely, the pitch value in the distal strain relief section 110 may begin with the pitch value $PV_2$ at the intermediate section 118 and end toward the distal end 108 with the pitch value $PV_3$ on the order of around 0.120 or 0.150 or so. It will be appreciated that pitch is used conventionally to indicate length for one revolution. It will also be appreciated that pitch values associated with the proximal strain relief section 106 and the distal strain relief section 110 can assume a series of incrementally increasing or decreasing pitches according to conventional definitions of pitch value or, as used in the present application, the pitch value may be, effectively, an intaneous pitch.

In such embodiments the pitch value $PV_2$ in the intermediate section 118 is substantially constant and is less than the pitch values $PV_1$ and $PV_3$. As mentioned above, in some embodiments the pitch values $PV_1$ and $PV_3$ may be equalized at a value of around 0.120 or 0.150 or so. Because the intermediate section 118 passes through the section of a scope (such as a bronchoscope or endoscope) associated with the flexible needle 102 that entails the highest degree of flexibility, in various embodiments the substantially constant pitch value $PV_2$ suitably is less than the pitch values $PV_1$ and $PV_3$. In some embodiments, the pitch value $PV_2$ may be on the order of around 0.040, 0.060, 0.080, or the like, as desired for a particular application.

It will be appreciated that with high angulations of the flexible needle 102 achieved due to increased flexibility imparted by the spiral cut 116 and choice of material and gauge, the tubing 114 is under compression or tension stress. It will further be appreciated that the stress is the greatest at both ends (that is, the proximal end 104 and the distal end 108) where the spiral cut 116 ends and the flexible needle 102 becomes inflexible (solid) again because the tubing 114 needs to go past the spiral cut 116 to avoid shunt creation and ensure proper coverage. It will be appreciated that overly high stresses where the spiral cut 116 ends (for example, if the flexible needle 102 is too flexible at the ends of the spiral cut 116) can lead to tearing or cracking of the tubing 114, thereby possibly helping lead to creation of a shunt and the resultant loss of vacuum, which can adversely impact ability of the flexible needle assembly 500 to aspirate tissue.

To that end, pitch value at the ends of the spiral cut 116 in the proximal strain relief section 106 and at the end of the spiral cut 116 in the distal strain relief section 110 is selected to have a value that is sufficiently high to provide a suitably low amount of flexibility (or, conversely, a suitable amount of rigidity) to mitigate strain on the tubing 114, thereby helping to protect the tubing 114. The localized stress experienced by the tubing 114 at the proximal end 104 and the distal end 108 is mitigated by the creation of stress relieving transition zones (that is, the proximal strain relief section 106 and the distal strain relief section 110) between the flexible portion (that is, the intermediate section 118) and the uncut (solid) portion of the needle 102 beyond the ends of the spiral cut 116. The continuously variable pitch of the spiral cut 116 that gets progressively bigger as it moves away from the intermediate section 118 (which is provided for increased needle flexibility) to the proximal end 104 and the distal end 108 has the effect of spreading the difference in stress over a longer area and, simultaneously, gradually reducing the stress to lower levels. As a result, the continuously variable pitch of the spiral cut 116 in the proximal strain relief section 106 and the distal strain relief section 110 can help to reduce stress concentrations due to high strain and can, therefore, help to mitigate strain on the tubing 114, thereby helping to protect the tubing 114.

It will be appreciated that the length of the stress relief transition zones (that is, the proximal strain relief section 106 and the distal strain relief section 110) can vary in length and gradation of pitch value depending on a desired amount of flexibility for the flexible needle 102. That is, a more rigid needle does not need as much strain relief compared to a highly flexible needle. Therefore, the appropriate amount of strain relief is needle dependent and can be adjusted accordingly.

Regarding column strength, in some embodiments a pitch value $PV_2$ of around 0.050 in the intermediate section 118 may correlate to selection of a high flexibility needle. In some other embodiments a pitch value $PV_2$ of around 0.080 in the intermediate section 118 may correlate to selection of a medium flexibility needle. In some other embodiments a pitch value $PV_2$ of around 0.110 in the intermediate section 118 may correlate to selection of a low flexibility needle. However, it will be appreciated that flexibility, gauge, and type of the flexible needle may be selected as desired for a particular application. Thus, it will be further appreciated that selection of the substantially constant pitch value $PV_2$ in the intermediate section 118 can help tune flexibility of the flexible needle assembly 500 to match flexibility requirements of a scope (such as a bronchoscope or endocope) associated with the flexible needle assembly 500.

In some embodiments it may be desirable to enhance echogenicity of the flexible needle assembly 500, especially in the vicinity of the piercing tip 120, in order to increase visibility of the piercing tip 120 by an imaging system. In such cases, if desired the flexible needle 102 may include echogenic enhancement features in the vicinity of the distal end 108. Given by way of non-limiting example, in some embodiments the flexible needle 102 may define scribe lines 122 in a region that may include portions of the intermediate section 118 and the proximal strain relief section 110.

Following are a series of flowcharts depicting implementations. For ease of understanding, the flowcharts are organized such that the initial flowcharts present implementations via an example implementation and thereafter the following flowcharts present alternate implementations and/or expansions of the initial flowcharts as either sub-component operations or additional component operations building on one or more earlier-presented flowcharts. Those having skill in the art will appreciate that the style of presentation utilized herein (that is, beginning with a presentation of a flowchart presenting an example implementation and thereafter providing additions to and/or further details in subsequent flowcharts) generally allows for a rapid and easy understanding of the various process implementations.

Figure 6A:
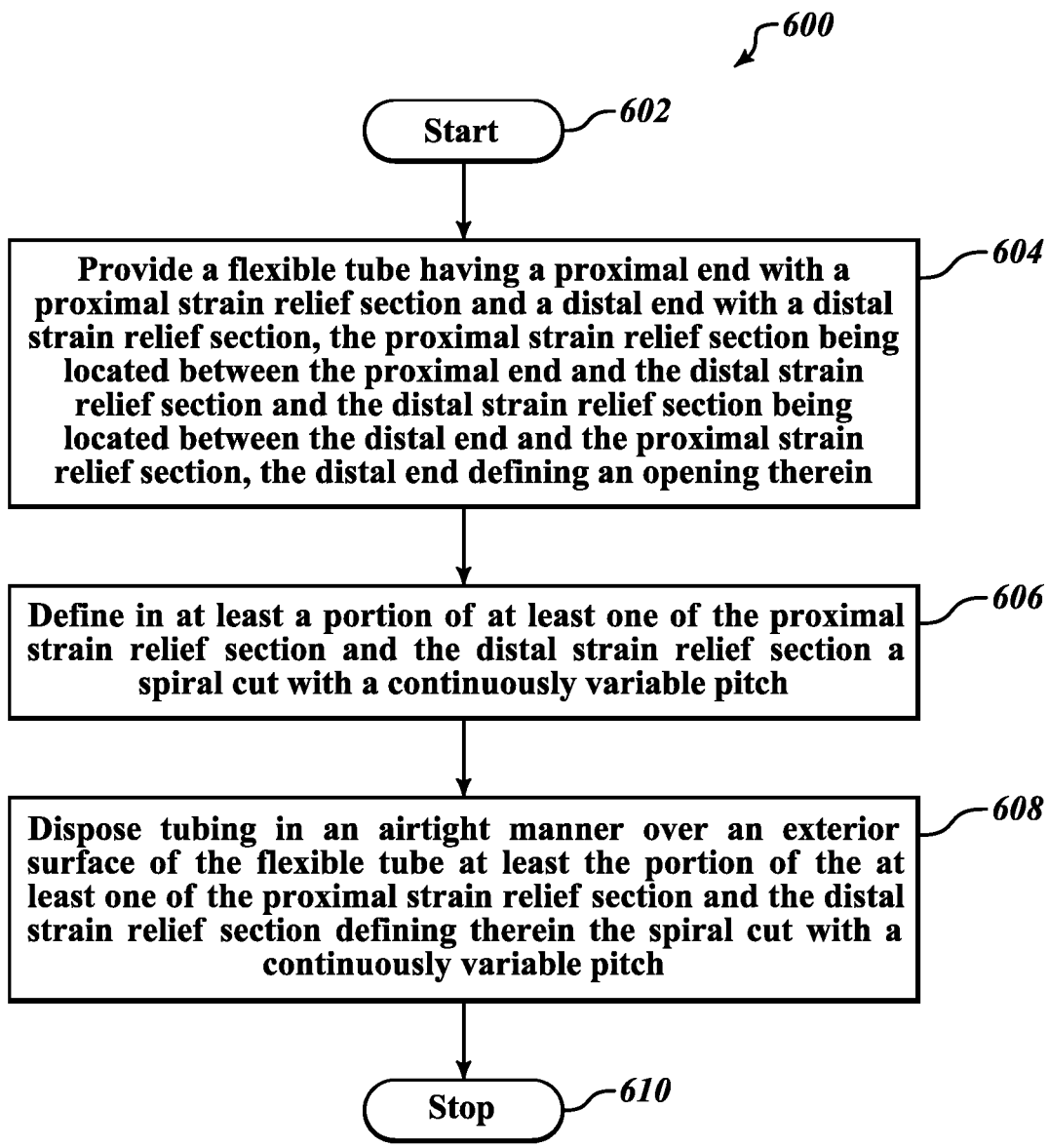
FIG. 6A is a flowchart of an illustrative method of fabricating a flexible tube assembly.

Referring now to FIG. 6A, an illustrative method 600 of fabricating a flexible tube assembly is provided. It will be appreciated that embodiments of the method 600 may be suitable for fabricating, without limitation, various embodiments of the flexible tube assembly 100 (FIGS. 1, 2A-2D, 3A, 3B, and 4). The method 600 starts at a block 602. At a block 604 a flexible tube having a proximal end with a proximal strain relief section and a distal end with a distal strain relief section is provided, the proximal strain relief section being located between the proximal end and the distal strain relief section and the distal strain relief section being located between the distal end and the proximal strain relief section, the distal end defining an opening therein. At a block 606 a spiral cut with a continuously variable pitch is defined in at least a portion of at least one of the proximal strain relief section and the distal strain relief section. At a block 608 tubing is disposed in an airtight manner over an exterior surface of the flexible tube at least the portion of the at least one of the proximal strain relief section and the distal strain relief section defining therein the spiral cut with a continuously variable pitch. The method 600 stops at a block 610.

In various embodiments, defining in at least a portion of at least one of the proximal strain relief section and the distal strain relief section the spiral cut with a continuously variable pitch at the block 606 may be performed via a laser cutting process.

In various embodiments and referring additionally to FIG. 6B, disposing tubing in an airtight manner over an exterior surface of the flexible tube from the proximal end to the distal end at the block 608 may include disposing heatshrink tubing in an airtight manner over an exterior surface of the flexible tube from the proximal end to the distal end at a block 612.

Figure 7A:
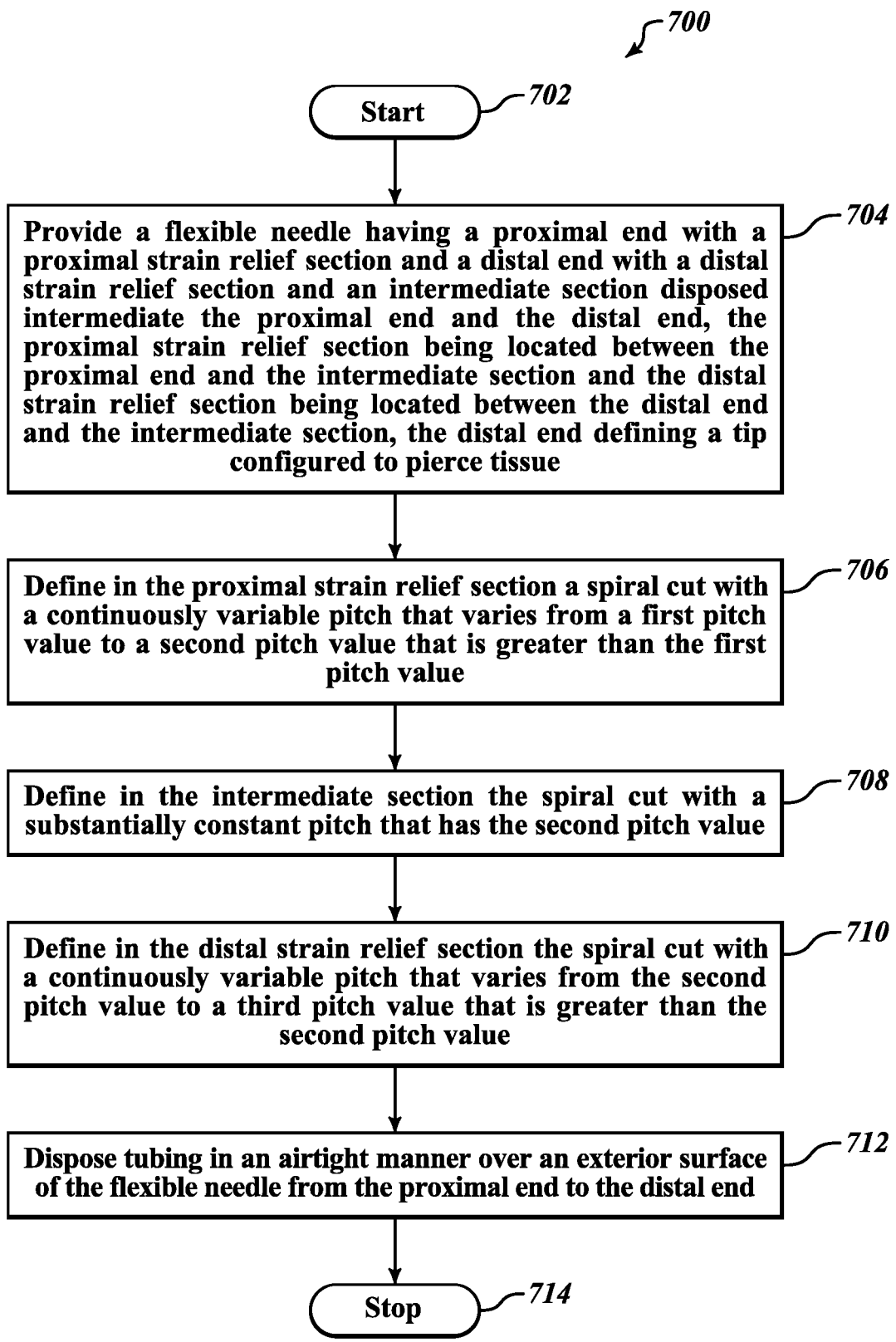
FIG. 7A is a flowchart of an illustrative method of fabricating a flexible needle assembly.

Referring now to FIG. 7A, an illustrative method 700 of fabricating a flexible needle assembly is provided. It will be appreciated that embodiments of the method 700 may be suitable for fabricating, without limitation, various embodiments of the flexible tube assembly 100 that is configured as a flexible needle assembly (FIG. 4) and the flexible needle assembly 500 (FIG. 5). The method 700 starts at a block 702. At a block 704 a flexible needle having a proximal end with a proximal strain relief section and a distal end with a distal strain relief section and an intermediate section disposed intermediate the proximal end and the distal end is provided, the proximal strain relief section being located between the proximal end and the intermediate section and the distal strain relief section being located between the distal end and the intermediate section, the distal end defining a tip configured to pierce tissue. At a block 706 a spiral cut with a continuously variable pitch that varies from a first pitch value to a second pitch value that is greater than the first pitch value is defined in the proximal strain relief section. At a block 708 the spiral cut is defined in the intermediate section with a substantially constant pitch that has the second pitch value. At a block 710 the spiral cut is defined in the distal strain relief section with a continuously variable pitch that varies from the second pitch value to a third pitch value that is greater than the second pitch value. At a block 712 tubing is disposed in an airtight manner over an exterior surface of the flexible needle from the proximal end to the distal end. The method 700 stops at a block 714.

In various embodiments defining a spiral cut at the blocks 706, 708, and 710 may be performed via a laser cutting process.

In various embodiments and referring additionally to FIG. 7B, disposing tubing in an airtight manner over an exterior surface of the flexible needle from the proximal end to the distal end at the block 712 may include disposing heatshrink tubing in an airtight manner over an exterior surface of the flexible needle from the proximal end to the distal end at a block 716.

Figure 8:
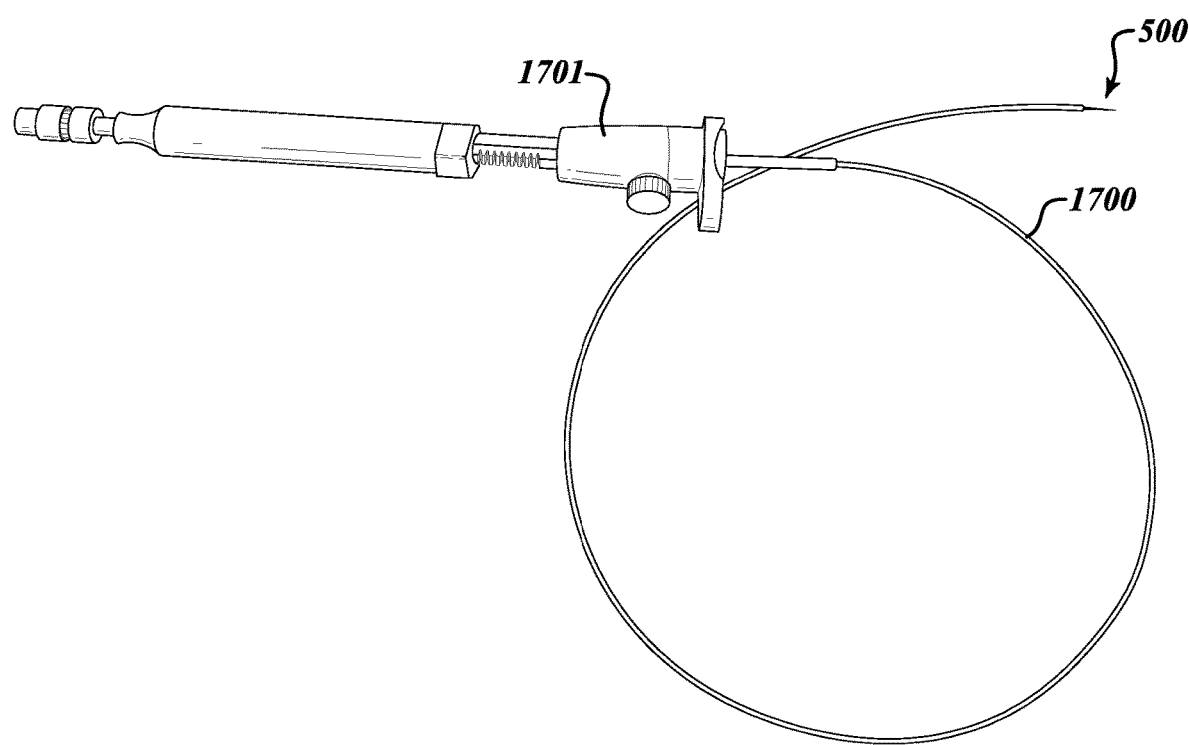
FIG. 8 is an illustration of a handle that may be used to manipulate and control embodiments of flexible needle assemblies described herein.

Referring now to FIG. 8, an illustrative handle 1701 may be used to manipulate and control embodiments of the flexible needle assembly 500 described herein. The handle 1701 suitably is connected to a catheter 1700 with a flexible needle hypotube therein, and the handle 1701 can control extension of the flexible needle assembly 500 from the catheter 1700.

Figure 9:
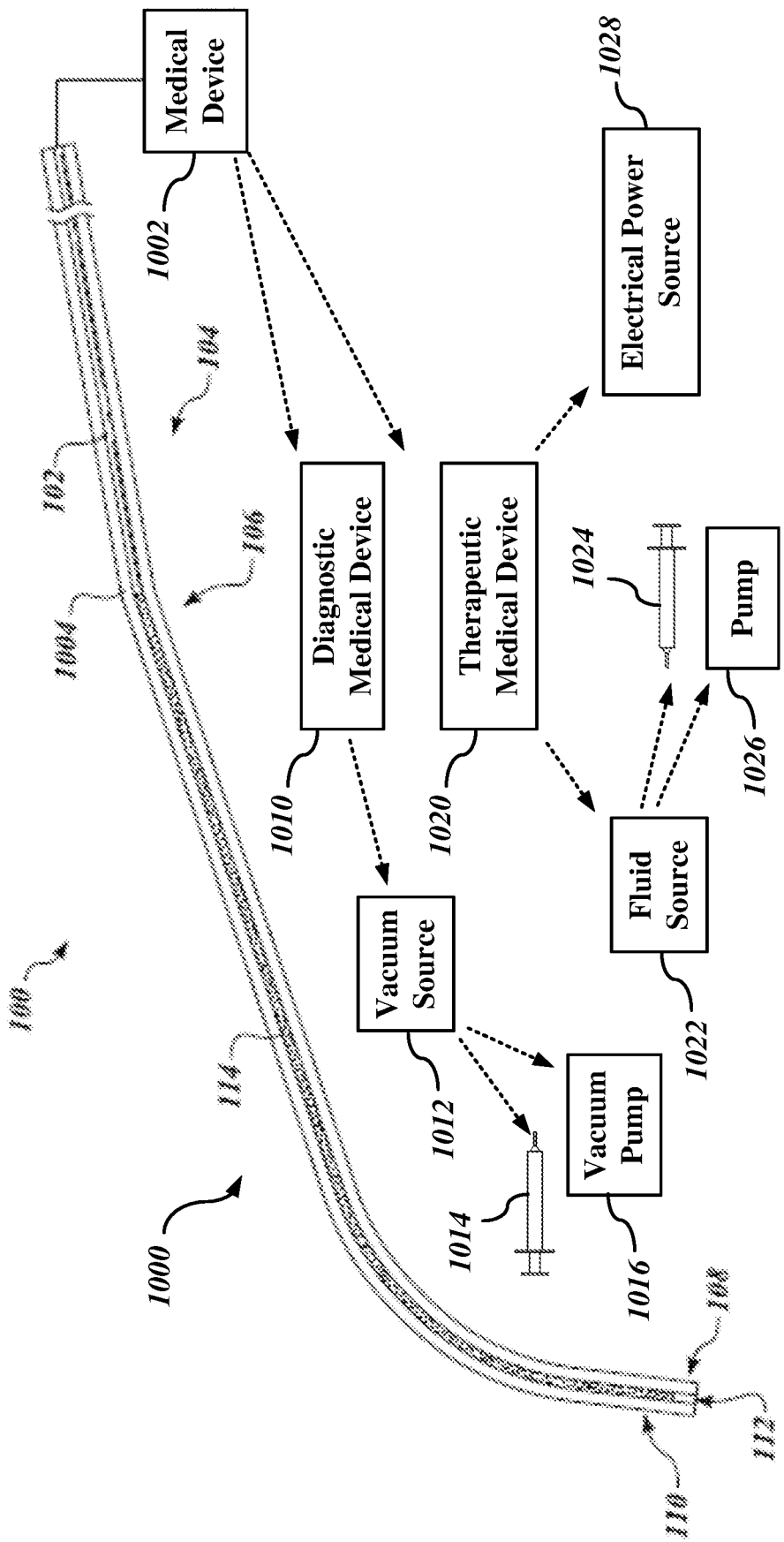
FIG. 9 is a perspective view in partial schematic form of a system that includes the flexible tube assembly of FIG. 1.

In some other embodiments and referring now to FIG. 9, an illustrative system 1000 is provided. In various embodiments and given by way of overview, the system 1000 includes the flexible tube assembly 100 and a medical device 1002 that is operatively coupled to the flexible tube 102.

Given by way of illustration only and not of limitation, in various embodiments the system 1000 includes a sheath 1004. The flexible tube assembly 100 is disposed in the sheath 1004. In various embodiments, the sheath 1004 is made of a suitable material for medical use in a body, such as a plastic, PTFE, or the like.

As discussed above and in various embodiments of the flexible tube assembly 100, the flexible tube 102 has the proximal end 104 with the proximal strain relief section 106 and the distal end 108 with the distal strain relief section 110. The proximal strain relief section 106 is located between the proximal end 104 and the distal strain relief section 110 and the distal strain relief section 110 is located between the distal end 108 and the proximal strain relief section 106. The distal end 108 defines the opening 112 therein. At least a portion of the proximal strain relief section 106 and/or the distal strain relief section 110 defines therein the spiral cut (not shown in FIG. 9) having a continuously variable pitch. The tubing 114 is disposed in an airtight manner over an exterior surface of the flexible tube 102 from at least the portion of the at least one of the proximal strain relief section and the distal strain relief section defining therein the spiral cut with a continuously variable pitch.

The medical device 1002 is operatively coupled to the flexible tube 102. In various embodiments, the medical device 1002 may include a diagnostic medical device 1010 having a diagnostic mode or a therapeutic medical device 1020 having a therapeutic mode.

In some embodiments in which the medical device 1002 includes a diagnostic medical device 1010 having a diagnostic mode, the system 1000 may be configured for aspiration of a sample from a site of interest. In such embodiments, the flexible tube 102 is configured as a flexible needle (such as in a manner as discussed above with reference to FIGS. 4 and 5). Also, in such embodiments the diagnostic medical device 1010 suitably includes a vacuum source 1012, such as a syringe 1014 or a vacuum pump 1016.

As discussed above, in some other embodiments the medical device 1002 may include a therapeutic medical device 1020 having a therapeutic mode. In some such embodiments the therapeutic medical device 1020 may include a fluid source 1022, such as a syringe 1024 or a pump 1026. In such embodiments, the fluid may include medicine, saline solution, or the like.

In some other such embodiments, the system 1000 may be configured for use in ablation of tissue. In such embodiments, the flexible tube 102 is configured as an electrode and the therapeutic medical device 1020 includes an electrical power source 1028. The system 1000 may be configured as a monopole system, in which the flexible tube 102 is a monopole electrode and an electrically-conductive plate (not shown) placed under a patient (not shown) functions as another electrode. Alternately, the system 1000 may be configured as a bipolar system, in which the flexible tube 102 is a primary electrode and a secondary electrode (not shown) is deployed to the vicinity of the tissue to be ablated.

It will be appreciated that the present descriptions of the biopsy systems, apparatuses, and methods described herein as being used in a lung and for lung nodules are not limiting, and that these embodiments may be used for biopsying, navigating, and locating areas of interest in other locations on a patient, including gastric, endoscopic, or other suitable locations. Similarly, a bronchoscope is not necessary, and other suitable devices capable of accommodating the embodiments described herein may also be used, including without limitation various endoscopes or laparoscopic cannulas.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. A flexible tube assembly comprising:
 a flexible tube having a proximal end with a proximal strain relief section and a distal end with a distal strain relief section, wherein the proximal strain relief section and the distal strain relief section are contiguous, with the proximal strain relief section extending from the proximal end to the distal strain relief section and the distal strain relief section extending from the distal end to the proximal strain relief section, the distal end defining an opening therein, wherein:
 the proximal strain relief section defines therein a spiral cut with a first continuously variable pitch that one of continuously increases and decreases from a first pitch value adjacent the proximal end to a second pitch value that is different from the first pitch value at a location adjacent to the distal end; and
 the distal strain relief section defines therein the spiral cut with a second continuously variable pitch that one of increases and decreases oppositely to the first continuously variable pitch; and
 tubing disposed in an airtight manner over an exterior surface of at least the portion of the at least one of the proximal strain relief section and the distal strain relief section defining therein the spiral cut.

2. The tube assembly of claim 1, wherein the tubing includes heatshrink tubing.

3. The tube assembly of claim 1, wherein the distal end defines a tip configured to pierce tissue.

4. A system comprising:
 a sheath;
 a flexible tube assembly disposed in the sheath, the flexible tube assembly including:
 a flexible tube having a proximal end with a proximal strain relief section and a distal end with a distal strain relief section, wherein the proximal strain relief section and the distal strain relief section are contiguous, with the proximal strain relief section extending from the proximal end to the distal strain relief section and the distal strain relief section extending from the distal end to the proximal strain relief section, the distal end defining an opening therein, wherein:
 the proximal strain relief section defines therein a spiral cut with a first continuously variable pitch that one of continuously increases and decreases from a first pitch value adjacent the proximal end to a second pitch value that is different from the first pitch value at a location adjacent to the distal end; and
 the distal strain relief section defines therein the spiral cut with a second continuously variable pitch that one of increases and decreases oppositely to the first continuously variable pitch;
 tubing disposed in an airtight manner over an exterior surface of at least the portion of the at least one of the proximal strain relief section and the distal strain relief section defining therein the spiral cut; and
 a medical device operatively coupled to the flexible tube.

5. The system of claim 4, wherein the tubing includes heatshrink tubing.

6. The system of claim 4, wherein the medical device includes a diagnostic medical device.

7. The system of claim 6, wherein:
 the flexible tube is configured as a flexible needle; and
 the diagnostic medical device includes a vacuum source.

8. The system of claim 7, wherein the vacuum source includes a device chosen from a syringe and a vacuum pump.

9. The system of claim 4, wherein the medical device includes a therapeutic medical device.

10. The system of claim 9, wherein the therapeutic medical device includes a fluid source.

11. The system of claim 9, wherein:
 the flexible tube is configured as an electrode; and
 the therapeutic medical device includes an electrical power source.

* * * * *